(12) United States Patent
Hernandez

(10) Patent No.: US 6,530,479 B2
(45) Date of Patent: Mar. 11, 2003

(54) HOUSING FOR SUTURING TOOLS

(76) Inventor: Alejandro Hernandez, 3924 E. Michigan Ave., Los Angeles, CA (US) 90063

( * ) Notice: Subject to any disclaimer, the term of this patent is extended or adjusted under 35 U.S.C. 154(b) by 91 days.

(21) Appl. No.: 09/901,770

(22) Filed: Jul. 10, 2001

(65) Prior Publication Data

US 2003/0010659 A1 Jan. 16, 2003

(51) Int. Cl.[7] .............................................. B65D 85/24
(52) U.S. Cl. ...................... 206/572; 206/63.3; 206/370; 206/380; 206/570; 220/553; 220/661
(58) Field of Search ....................... 206/63.3, 363–366, 206/370, 380, 382, 383, 438, 570–572; 220/503–505, 553, 555, 661; 422/300, 310

(56) References Cited

U.S. PATENT DOCUMENTS

| | | | | |
|---|---|---|---|---|
| 2,397,322 A | * | 3/1946 | Markle, Jr. ................. | 220/555 |
| 2,865,501 A | * | 12/1958 | Smart, Jr. et al. .......... | 206/63.3 |
| 4,050,894 A | * | 9/1977 | Genis .......................... | 206/363 |
| 5,207,321 A | * | 5/1993 | Jones .......................... | 220/553 |
| 5,245,117 A | * | 9/1993 | Withers et al. .............. | 206/366 |
| 5,447,237 A | * | 9/1995 | Carter et al. ................. | 206/570 |
| 5,590,774 A | * | 1/1997 | Roberts ....................... | 206/366 |
| 5,968,458 A | * | 10/1999 | Shaikho ...................... | 206/370 |
| 2002/0020646 A1 | * | 2/2002 | Groth et al. ................. | 206/366 |
| 2002/0074525 A1 | * | 6/2002 | White et al. ................. | 206/365 |

* cited by examiner

Primary Examiner—Jim Foster
(74) Attorney, Agent, or Firm—Goldstein & Lavas, P.C.

(57) ABSTRACT

A housing for suturing tools including a cylindrical housing having an upper end, a lower end, a cylindrical side wall therebetween, and a hollow interior. The cylindrical housing has a central dividing wall disposed within the hollow interior extending between the upper and lower ends. The central dividing wall equally divides the cylindrical housing into a first section and a second section. The cylindrical side wall of the first section has an opening therethrough positioned intermediate the upper and lower ends thereof. The cylindrical side wall of the second section has at least one opening therethrough adjacent to the lower end thereof.

4 Claims, 2 Drawing Sheets

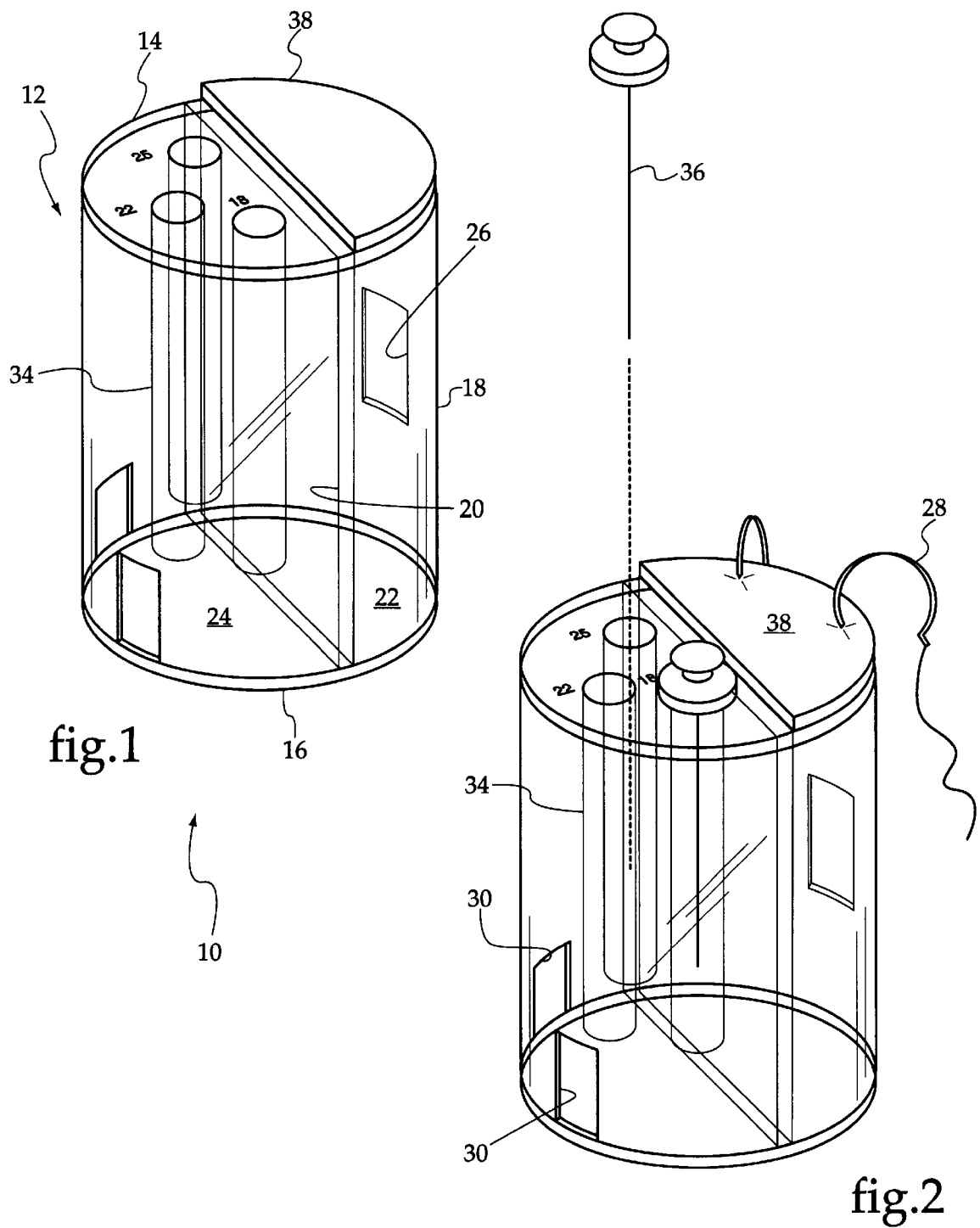

HOUSING FOR SUTURING TOOLS

BACKGROUND OF THE INVENTION

The present invention relates to a housing for suturing tools and more particularly pertains to safely housing suturing tools in one place for easy access.

The use of medical safety devices is known in the prior art. More specifically, medical safety devices heretofore devised and utilized for the purpose of facilitating the safe use of medical instruments are known to consist basically of familiar, expected and obvious structural configurations, notwithstanding the myriad of designs encompassed by the crowded prior art which have been developed for the fulfillment of countless objectives and requirements.

By way of example, U.S. Pat. No. 5,469,964 to Bailey discloses a device for unsheathing and resheathing a series of needles. U.S. Pat. No. 4,989,307 to Sharpe discloses a device for removing and disposing needles with risk of contamination. U.S. Pat. No. 5,607,403 to Kretzschmar and U.S. Pat. No. 5,564,565 to Yamada disclose various safety devices for safely disposing needles.

While these devices fulfill their respective, particular objective and requirements, the aforementioned patents do not describe a housing for suturing tools for safely housing suturing tools in one place for easy access.

In this respect, the housing for suturing tools according to the present invention substantially departs from the conventional concepts and designs of the prior art, and in doing so provides an apparatus primarily developed for the purpose of safely housing suturing tools in one place for easy access.

Therefore, it can be appreciated that there exists a continuing need for a new and improved housing for suturing tools which can be used for safely housing suturing tools in one place for easy access. In this regard, the present invention substantially fulfills this need.

SUMMARY OF THE INVENTION

In the view of the foregoing disadvantages inherent in the known types of medical safety devices now present in-the prior art, the present invention provides an improved housing for suturing tools. As such, the general purpose of the present invention, which will be described subsequently in greater detail, is to provide a new and improved housing for suturing tools which has all the advantages of the prior art and none of the disadvantages.

To attain this, the present invention essentially comprises a cylindrical housing having an upper end, a lower end, a cylindrical side wall therebetween, and a hollow interior. The cylindrical housing has a central dividing wall disposed within the hollow interior extending between the upper and lower ends. The central dividing wall equally divides the cylindrical housing into a first section and a second section. The cylindrical side wall of the first section has an opening therethrough positioned intermediate the upper and lower ends thereof. The cylindrical side wall of the second section has a pair of openings therethrough adjacent to the lower end thereof. Three tubular casings are disposed within the second section of the cylindrical housing. The casings each have an open upper end disposed within the upper end of the second section. The casings each have a closed lower end. A soft pad is secured to the upper end of the first section of the cylindrical housing.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved housing for suturing tools which has all the advantages of the prior art medical safety devices and none of the disadvantages.

It is another object of the present invention to provide a new and improved housing for suturing tools which may be easily and efficiently manufactured and marketed.

It is a further object of the present invention to provide a new and improved housing for suturing tools which is of durable and reliable construction.

An even further object of the present invention is to provide a new and improved housing for suturing tools which is susceptible of a low cost of manufacture with regard to both materials and labor, and which accordingly is then susceptible of low prices of sale to the consuming public, thereby making such a housing for suturing tools economically available to the buying public.

Even still another object of the present invention is to provide a new and improved housing for suturing tools for safely housing suturing tools in one place for easy access.

Lastly, it is an object of the present invention to provide a new and improved housing for suturing tools including a cylindrical housing having an upper end, a lower end, a cylindrical side wall therebetween, and a hollow interior. The cylindrical housing has a central dividing wall disposed within the hollow interior extending between the upper and lower ends. The central dividing wall equally divides the cylindrical housing into a first section and a second section. The cylindrical side wall of the first section has an opening therethrough positioned intermediate the upper and lower ends thereof. The cylindrical side wall of the second section has at least one opening therethrough adjacent to the lower end thereof.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of the preferred embodiment of the housing for suturing tools constructed in accordance with the principles of the present invention.

FIG. 2 is a perspective view of the present invention illustrated in use.

The same reference numerals refer to the same parts through the various figures.

DESCRIPTION OF THE PREFERRED EMBODIMENT

Figure 3:
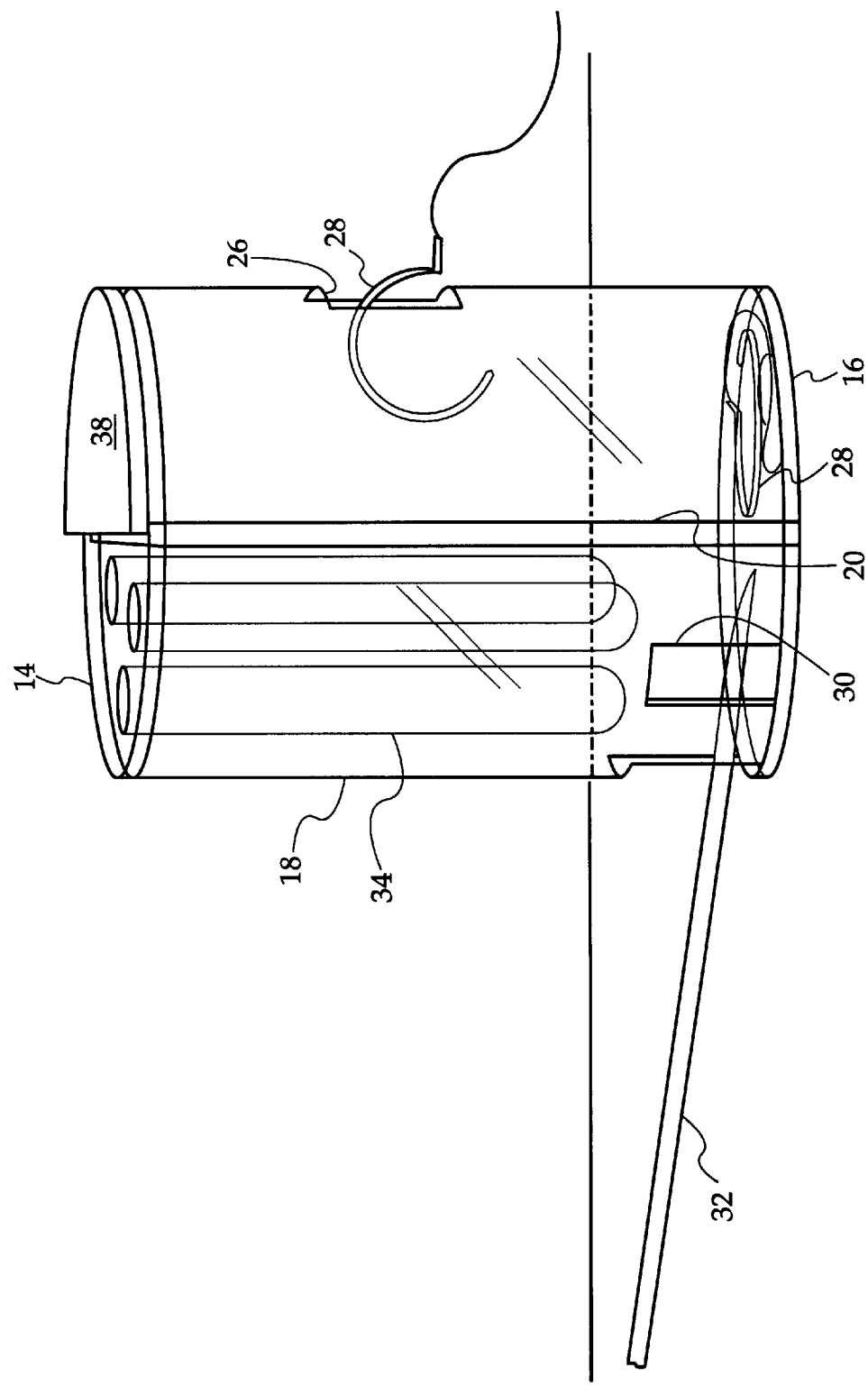
FIG. 3 is a side view of the present invention illustrated in use.

With reference now to the drawings, and in particular, to FIGS. 1 through 3 thereof, the preferred embodiment of the new and improved housing for suturing tools embodying the principles and concepts of the present invention and generally designated by the reference number 10 will be described.

Specifically, it will be noted in the various figures that the device relates to a housing for suturing tools for safely housing suturing tools in one place for easy access. In its broadest context, the device consists of a cylindrical housing, three tubular casings, and a soft pad. Such components are individually configured and correlated with respect to each other so as to attain the desired objective.

The cylindrical housing 12 has an upper end 14, a lower end 16, a cylindrical side wall 18 therebetween, and a hollow interior. The cylindrical housing 12 has a central dividing wall 20 disposed within the hollow interior extending between the upper and lower ends 14,16. The central dividing wall 20 equally divides the cylindrical housing 12 into a first section 22 and a second section 24. The dividing of the cylindrical housing 12 allows for the proper storage of different suturing instruments. The cylindrical side wall 18 of the first section 22 has an opening 26 therethrough positioned intermediate the upper and lower ends 14,16 thereof. The opening 26 allows used suture needles 28 to be placed therethrough after they have been used. The cylindrical side wall 18 of the second section 24 has a pair Of openings 30 therethrough adjacent to the lower end 16 thereof. The openings 30 allow for surgical instruments such as scissors and scalpels 32 to be placed therein whereby these instruments can be easily removed for a next use.

The three tubular casings 34 are disposed within the second section 24 of the cylindrical housing 12. The casings 34 each have an open upper end disposed within the upper end 14 of the second section 24. The casings 34 each have a closed lower end. The casings 34 are provided to contain hypodermic needles 36 therein. The three casings 34 are primarily used to hold three different gauged needles. Additionally, the casings 34 can be labeled to indicate which size needle is to be positioned therein.

The soft pad 38 is secured to the upper end 14 of the first section 22 of the cylindrical housing 12. The soft pad 38 is in the shape of semi-circle for use in providing a soft location for the placement of suture needles 28 while a physician is suturing.

The present invention is designed for a one time use after which it should be properly discarded. The present invention is designed to hold scalpels, scissors, hypodermic needles, and suturing needles that are used during a suturing procedure.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A housing for suturing tools for safely housing suturing tools in one place for easy access comprising, in combination:

a cylindrical housing having an upper end, a lower end, a cylindrical side wall therebetween, and a hollow interior, the cylindrical housing having a central dividing wall disposed within the hollow interior extending between the upper and lower ends, the central dividing wall equally dividing the cylindrical housing into a first section and a second section, the cylindrical side wall of the first section having an opening therethrough positioned intermediate the upper and lower ends thereof, the cylindrical side wall of the second section having a pair of openings therethrough adjacent to the lower end thereof;

three tubular casings disposed within the second section of the cylindrical housing, the casings each having an open upper end disposed within the upper end of the second section, the casings each having a closed lower end; and a soft pad secured to the upper end of the first section of the cylindrical housing.

2. A housing for suturing tools for safely housing suturing tools in one place for easy access comprising, in combination:

a cylindrical housing having an upper end, a lower end, a cylindrical side wall therebetween, and a hollow interior, the cylindrical housing having a central dividing wall disposed within the hollow interior extending between the upper and lower ends, the central dividing wall equally dividing the cylindrical housing into a first section and a second section, the cylindrical side wall of the first section having an opening therethrough positioned intermediate the upper and lower ends thereof, the cylindrical side wall of the second section having at least one opening therethrough adjacent to the lower end thereof.

3. The housing for suturing tools as set forth in claim 2, and further including a plurality of tubular casings disposed within the second section of the cylindrical housing, the casings each having an open upper end disposed within the upper end of the second section, the casings each having a closed lower end.

4. The housing for suturing tools as set forth in claim 2, and further including a soft pad secured to the upper end of the first section of the cylindrical housing.

* * * * *